(12) United States Patent
Gouch

(10) Patent No.: US 7,645,971 B2
(45) Date of Patent: Jan. 12, 2010

(54) IMAGE SCANNING APPARATUS AND METHOD

(75) Inventor: Martin Philip Gouch, Herts (GB)

(73) Assignee: FFEI Limited, Hertfordshire (GB)

( * ) Notice: Subject to any disclaimer, the term of this patent is extended or adjusted under 35 U.S.C. 154(b) by 0 days.

(21) Appl. No.: 12/016,298

(22) Filed: Jan. 18, 2008

(65) Prior Publication Data

US 2009/0185167 A1 Jul. 23, 2009

(51) Int. Cl.
G02B 27/64 (2006.01)
G02B 21/00 (2006.01)

(52) U.S. Cl. .................... 250/201.2; 359/368
(58) Field of Classification Search .......... 250/201.2, 250/201.3, 201.8, 201.1–201.9; 359/368, 359/382, 383, 391–394; 356/237.1–237.5, 356/28, 28.5, 72, 73
See application file for complete search history.

(56) References Cited

U.S. PATENT DOCUMENTS

| | | | |
|---|---|---|---|
| 4,099,051 A * | 7/1978 | Gugliotta .................. 250/236 |
| 4,812,643 A * | 3/1989 | Talbot ..................... 250/222.1 |
| 4,844,617 A * | 7/1989 | Kelderman et al. ......... 356/624 |
| 5,248,876 A | 9/1993 | Kerstens et al. |
| 5,394,205 A | 2/1995 | Ochiai et al. |
| 5,446,276 A | 8/1995 | Iyoda et al. |
| 5,659,390 A * | 8/1997 | Danko .................... 356/237.4 |
| 5,763,871 A | 6/1998 | Ortyn et al. |
| 5,912,699 A | 6/1999 | Hayenga et al. |
| 6,091,075 A * | 7/2000 | Shibata et al. ........... 250/559.44 |
| 6,580,502 B1* | 6/2003 | Kuwabara ................ 356/237.3 |
| 6,875,973 B2* | 4/2005 | Ortyn et al. .............. 250/201.3 |
| 7,015,418 B2 | 3/2006 | Cahill et al. |
| 7,109,459 B2* | 9/2006 | Kam et al. ................ 250/201.4 |
| 7,345,755 B2* | 3/2008 | Ogawa et al. ............ 356/237.5 |
| 2003/0067596 A1* | 4/2003 | Leonard ................. 356/237.1 |
| 2003/0160957 A1* | 8/2003 | Oldham et al. ............ 356/317 |
| 2004/0256538 A1 | 12/2004 | Olson et al. |
| 2005/0286800 A1 | 12/2005 | Gouch |
| 2006/0238847 A1 | 10/2006 | Gouch |
| 2007/0147673 A1* | 6/2007 | Crandall .................. 382/128 |

FOREIGN PATENT DOCUMENTS

| | | |
|---|---|---|
| DE | 200 16 490 U1 | 12/2000 |
| EP | 1 593 957 A1 | 11/2005 |
| WO | WO 01/37025 A1 | 5/2001 |

OTHER PUBLICATIONS

"Entering the Age of Fluorescence Imaging in Digital Slide Technology"; Hamamatsu Photonics K.K., Systems Division; 2006; Japan.

* cited by examiner

*Primary Examiner*—Georgia Y Epps
*Assistant Examiner*—Jennifer Bennett
(74) *Attorney, Agent, or Firm*—Sughrue Mion, PLLC

(57) ABSTRACT

An image scanning apparatus comprises a time delay integration sensor for obtaining first image information from a target and a scan device for causing relative motion between the time delay integration sensor and the target. The image scanning apparatus is characterized by detector array for obtaining second image information from a target, wherein the first image information corresponds to a first portion of light received from the target and the second image information corresponds to a second portion of light received from the target.

24 Claims, 10 Drawing Sheets

IMAGE SCANNING APPARATUS AND METHOD

FIELD OF THE INVENTION

The invention relates to an image scanning apparatus and method. In particular the invention relates to the capture of image information whilst using a time delay integration sensor.

BACKGROUND OF THE INVENTION

In the field of microscopes used for scanning biological samples and the like, there is often the problem of obtaining a suitable amount of light from the target or sample in order to build a comprehensive image of an area of interest. This is especially the case when capturing image information corresponding to fluorescing samples, wherein, due to the fluorescence, the amount of light reaching a conventional detector array is not enough to provide a clear image of the target. In the art, this problem is typically solved using a time delay integration (TDI) sensor. This sensor is adapted to integrate a plurality of captured images of the target to produce a high quality image.

A prior art image scanning device for use in capturing image information from fluorescent samples is shown in FIG. 1. This conventional image scanning apparatus 1 comprises a lens assembly 20, a lens 10 and a time delay integration (TDI) sensor 80 for use in capturing image information. Typically, certain molecules within a sample 30 are labeled with a fluorescent marker or "fluorophore" that enables items of interest to fluoresce; for example, cancer cells within a tissue sample may be selectively labeled with the fluorescent marker. To subsequently activate these fluorophore molecules and enable fluorescence, the sample 30 must be irradiated with light of a first wavelength. This light is commonly referred to as the excitation radiation 15 and will comprise light within a set spectral band, typically ultra-violet radiation. This radiation 15 may be produced using an exciter source 40 which emits white light 5 comprising wideband spectral electromagnetic (EM) radiation. Excitation filter 50 then filters this light so that only the spectral band making up the desired excitation radiation 15 is allowed to illuminate the sample 30. A dichroic beam splitter 60 is configured to reflect the excitation radiation 15 towards lens assembly 20, wherein the radiation 15 passes through the lens 10 before impinging upon the sample 30.

After impinging on the sample 30, the excitation radiation 15 excites the fluorescent molecules within the sample. These molecules then emit light 25 of a second wavelength or second spectral band, i.e. the fluorophore molecules fluoresce. Typically, this emitted light is within the visible spectrum. The light 25 emitted by the sample 30 then passes back through the lens assembly 20, wherein it is focused by the lens 10. After focusing, the emitted light 25 then continues to the dichroic beam splitter 60, which is configured to allow light of a second wavelength or within a second spectral band to pass through the beam splitter. After passing through the beam splitter 60 the emitted light 25 may be further filtered by emission filter 70. The emitted light 25 then impinges on the TDI sensor 80 and image information is captured.

One problem that exists with the apparatus shown in FIG. 1 is that the use of a TDI sensor 80 places limits upon the use of the microscope. As the TDI sensor typically integrates images of a particular area of the target, the system is sensitive to changes during the acquisition of each image used in the integration. This can then make activities such as focusing difficult to perform, as changes in focus cannot be made whilst capturing a particular image within the integrated set, as this would degrade the resultant integrated image.

In particular, when scanning biological samples and the like, it is often necessary to re-focus the objective lens rapidly in order to compensate for variations in thickness of a biological sample being inspected. The design of the TDI sensor makes it difficult to use the image information captured by the sensor to perform these focusing operations. Hence, there is a requirement for an image scanning apparatus using a TDI sensor that is able to rapidly refocus the objective lens in order to account for variations in biological samples.

SUMMARY OF THE INVENTION

In accordance with a first aspect of the present invention, there is provided an image scanning apparatus comprising a time delay integration sensor for obtaining first image information from a target; and a scan device for causing relative motion between the time delay integration sensor and the target; the image scanning apparatus characterized by: a detector array for obtaining second image information from a target; wherein the first image information corresponds to a first portion of light received from the target and the second image information corresponds to a second portion of light received from the target, the first and second portions being separated in at least one of the following ways: spatially, chromatically or temporally.

Through the use of a detector array in addition to the time delay integration (TDI) sensor, second image information may be captured without disturbing or interrupting the integration process of the TDI sensor. Hence, focus or spatial scans of the target may be performed whilst an image of a particular area of the target is captured with the TDI sensor.

For example the first and second portions may respectively correspond to at least one of: different spatial areas of the target; different wavelengths of light received from the target; and light received from the target at different time periods. Using the spatial, chromatic or temporal properties of the light received from the target to maintain the separation of the two sets of image information prevents the capture of the second image information from disturbing or interrupting the capture of the first image information.

In a particular embodiment the image scanning apparatus may further comprise a focusing device adapted to modify the focus between the time delay integration sensor and the target; and a processor adapted to control the focusing device; wherein the second image information is used by the processor to select a focus level for the focusing device. Hence, the separate second image information may be used to enable focusing operations that were not previously possible whilst obtaining first image information with a TDI sensor.

In another embodiment of the present invention the image scanning apparatus may further comprise a fluorescence exciter source configured to irradiate the target and cause the target to fluoresce. In this case the first image information may comprise an image of target fluorescence that requires a TDI sensor to obtain adequate light levels. By using a detector array, that may comprise a red, green, and blue (RGB) detector array, second image information not used to create an image of a fluorescing target may be used to permit operations not possible with fluorescence image information recorded by the TDI sensor. The exciter source may be configured to supply either epi-illumination or trans-illumination. A further source may also be optionally provided to allow both forms of illumination.

In a preferred embodiment the image scanning apparatus further comprises at least one light redirection device configured to redirect light from the target to at least one of the time delay integration sensor and the detector array. This light redirection device may be a dichroic beam splitter to chromatically separate the first and second image information or a mirror to spatially separate the first and second image information. This mirror may be an off axis mirror or may be located such that a central portion of the light received from the target is directed toward the TDI sensor and a peripheral portion of the light received from the target is directed toward the detector array. The light redirection device, TDI sensor and/or detector array may also alternatively be positioned to capture spatially separated first and second image information.

In one embodiment of the present invention the image scanning apparatus may comprise a line scan apparatus wherein the detector array and/or the TDI sensor is a linear detector array configured to capture a scan line of the target. In certain embodiments the optical path length from the target to the detector array may equal the optical path length from the target to the time delay integration sensor so that the level of focus for information captured by the TDI sensor is equal to the level of focus for information captured by the detector array. In other embodiments the optical path lengths may be different and this may be taken into account when calculating a focus position.

In accordance with a second aspect of the present invention there is provided a method of focusing an image scanning apparatus comprising:

capturing first image information of a target using a time delay integration sensor, the first image information corresponding to a first portion of light received from the target;

capturing second image information of the target using a detector array, the second image information corresponding to a second portion of light received from the target;

calculating a focus position for use in capturing the first image information using the second image information; and adjusting the focus of the image scanning apparatus according to the calculated focus position.

This method may be performed using the apparatus of the first aspect of the invention, thus increasing the benefits provided by the first aspect. As with the first aspect, the first and second portions may be separated in at least one of the following ways: spatially, chromatically or temporally. Temporal separation may involve using the detector array to perform a focus scan comprising the capture of second image information before a final image scan comprising the capture of first image information. In other embodiments first and second image information may be captured contemporarily or separately. The capture of second image information is preferably independent of the capture of first image information, however in other embodiments the two capture processes may be synchronized. When using fluorescence microscopy step a) may further comprise irradiating the target to enable the target to fluoresce, wherein the first image information comprises image information corresponding to the fluorescence of the target. Using this method focusing techniques designed to be used with a RGB line-scan image apparatus may also be used in fluorescence microscopy.

BRIEF DESCRIPTION OF THE DRAWINGS

Some examples of an image scanning apparatus and methods of controlling said apparatus will now be described with reference to the accompanying drawings, in which.

DETAILED DESCRIPTION OF THE EMBODIMENTS

Figure 2A:
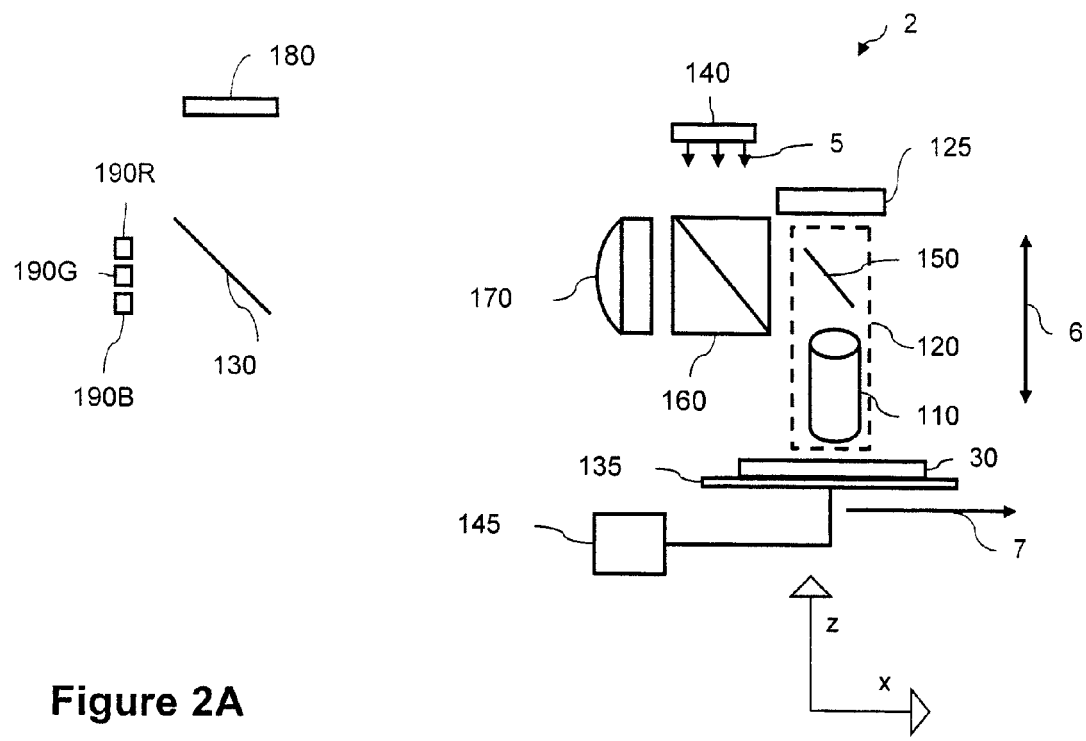
FIG. 2A is a schematic side view of an exemplary image scanning apparatus according to a first embodiment of the present invention.
Figure 2B:
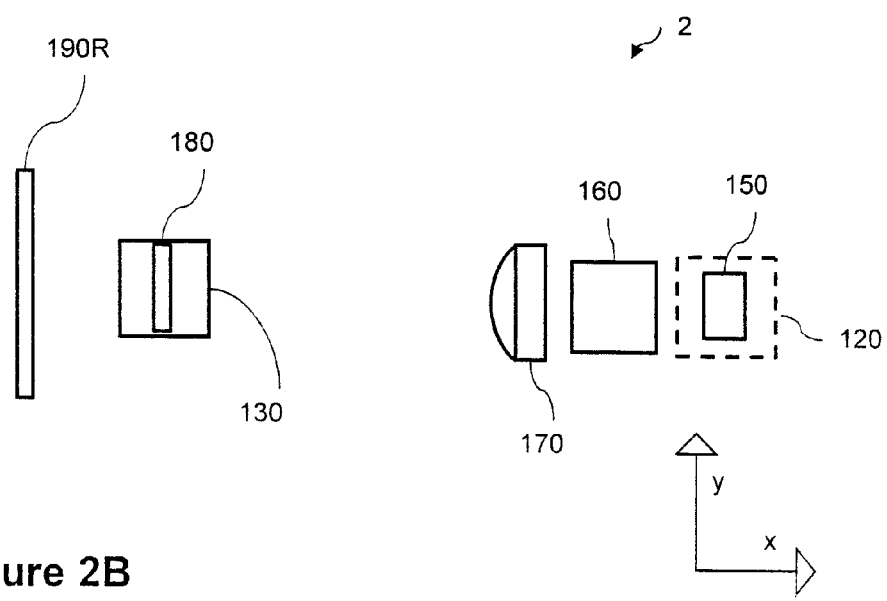
FIG. 2B is a plan of the first embodiment of the present invention.

An exemplary image scanning apparatus according to a first embodiment of the present invention is shown generally in FIGS. 2A and 2B. The image scanning apparatus 2 comprises a lens assembly 120 containing a lens 110. The lens assembly 120 acts as an adjustable focus system. A target or sample to be scanned 30 is positioned upon a platen 135 below the lens assembly 120.

In the present example, the lens assembly 120 is attached to a first drive mechanism 125 that enables the lens assembly 120 to be moved in the z-direction with respect to the target 30. In alternative embodiments, the lens assembly 120 may be fixed and the drive mechanism may be configured to move the target 30 in the z-direction. In a preferred embodiment the first drive mechanism comprises a linear actuator such as a voice coil actuator, wherein the linear actuator is configured to focus the lens through focusing movement 6. In the present example, the platen 135, upon which the target 30 is positioned, is then attached to a second drive mechanism 145 that is configured to move the target 30 in the x-direction to effect a scanning movement 7. Hence, focusing movement 6 allows the focus of the system to be adjusted and scanning movement 7 allows the image scanning apparatus to traverse the complete area of the target 30.

The image scanning apparatus 2 also comprises time delay integration (TDI) sensor 180. In the present example the TDI sensor 180 comprises a plurality of linear detector arrays adapted to record image information from the target 30. Each linear detector array is adapted to capture a "scan line" of the target 30, wherein a "scan line" comprises an image of whole or part of a particular area of the target 30 that extends in the y-direction. Typically, due to the design of each linear detector, each "scan line" will comprise an elongate image strip of size n*m pixels; wherein m=1 and n>>m. A plurality of "scan lines" may then be combined to generate a larger image of whole or part of the target. The scanning movement 7 enables the TDI sensor 180 to record a number of different "scan lines" during traversal of the target 30 in the x-direction. In more complex embodiments, the TDI sensor 180 is configured to capture an image of size 2048×128 pixels, each pixel covering an area of approximately 0.325 micrometers by 0.325 micrometers.

The exemplary image scanning apparatus shown in FIGS. 2A and 2B is adapted to record image information related to fluorescent samples. In such a case an exciter source 140 is provided to emit light or excitation radiation 5 of a first wavelength or spectral band. Commonly this excitation radiation 5 comprises ultra-violet radiation. In other embodiments of the present invention image information may be recorded from non-fluorescing samples. In such a case, the exciter source 140 may be used to illuminate the target or may be omitted.

Figure 1:
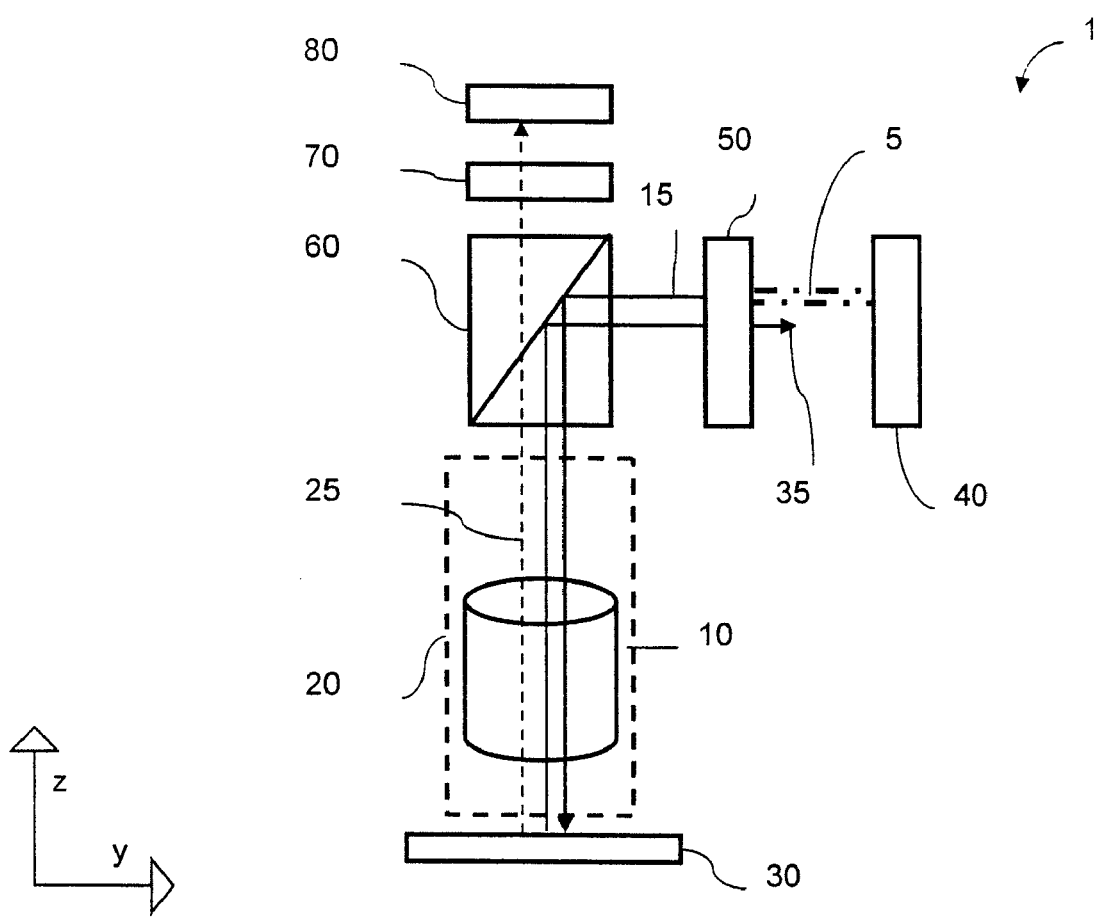
FIG. 1 is an prior art image scanning apparatus used in fluorescence microscopy.

Returning to FIG. 2A, after emission by exciter source 140, the excitation radiation 5 is reflected by dichroic beam splitter 160 toward the lens assembly 120 and light redirection device 150. When using fluorescing samples, the dichroic beam splitter 160 is typically adapted to reflect radiation corresponding to the particular wavelength or spectral band of the excitation radiation 5, whilst allowing other spectral bands to pass through the beam splitter 160 unaltered. In other embodiments the dichroic beam splitter 160 may alternatively comprise a dichroic mirror. In some embodiments excitation source 140 may further comprise a wide band emitter 14 and a filter 15 as is shown in FIG. 1. In alternative embodiments beam splitter 160 or light redirection device 150 may comprise a specific coating to provide the effect of filter 15. Light redirection device 150 typically comprises a mirror that is mounted within the lens assembly 120. This mirror is adapted to reflect light in and out of the lens assembly 120. Light redirection device 150 typically allows the image scanning apparatus to be reduced in height. In alternative embodiments, wherein horizontal space is limited, light redirection device 150 may be omitted and elements 130, 140, and 160 to 190 may be rotated clockwise by ninety degrees to produce an apparatus that extends in the z-direction or further light redirection devices may be employed as known in the art to reduce the size of the apparatus while retaining the required optical path length.

On arriving at the target the excitation radiation 5 excites the fluorescent fluorophore molecules within the target 30 and enables the emission of fluorescent light of a second wavelength or spectral band. This light radiation of a second wavelength or spectral band passes back up through lens 110 and is reflected towards the dichroic beam splitter 160 by the redirection device 150. Dichroic splitter 160 is then configured to allow the emitted light to pass through the splitter 160 without reflection and thus continue through tube lens 170 toward light redirection device 130. The tube lens 170 is provided to correctly focus the light emerging from the lens assembly 120 so that it may impinge correctly on the light detection sensors such as TDI sensor 180.

In addition, the image scanning apparatus of the present invention further comprises a second light detector 190. In the present example, this light detector 190 comprises three separate arrays: a red line scan detector array 190R, a green line scan detector array 190G and a blue line scan detector array 190B; each line scan detector array being adapted to record image information from the target 30. Typically, this image information comprises a "scan line" of the target, as described previously. Red, green and blue (RGB) light from the target 30 passes through lens 110 and is directed by light redirection device 150 to dichroic beam splitter 160. The dichroic beam splitter 160 is adapted to allow this RGB light to pass through the splitter without reflection. After passing through dichroic beam splitter 160, the light is then further focused through tube lens 170 before impinging on light redirection device 130.

In the embodiment shown in FIGS. 2A and 2B, light redirection device 130 comprises a mirror. This mirror is adapted to reflect emitted light from the target 30 into TDI sensor 180. Light redirection device 130 may optionally comprise a special coating to provide the functionality of an emission filter if this is required, i.e. to only redirect light within a chosen spectral band toward the TDI sensor 180. In other cases an emission filter, similar to filter 80 in FIG. 1, may be placed between dichroic beam splitter 160 and tube lens 170. As can be seen in FIG. 2B, the mirror only extends across a portion of the detector arrays 190 in the y-direction. Typically, the mirror 130 extends a distance in the y-direction that is equal to, or greater than, the length of the TDI sensor 180 in the y-direction. This arrangement allows light to pass either side of the mirror 130 and impinge upon the detector arrays 190. Hence, image information corresponding to red, green and blue wavelengths of light is recorded by respective line scan arrays 190R, 190G and 190B.

In the first embodiment shown in FIG. 2B the central portion of a captured scan line is directed toward TDI sensor 180, whereas a peripheral portion of a captured scan line is directed toward the RGB detector arrays 190. Typically, the central portion and the peripheral portion correspond to mutually exclusive spatial areas upon a strip of the target that extends in the y-direction. Hence, the first embodiment shows an apparatus wherein the image portion captured by the TDI sensor 180 and the detector array 190 correspond to spatially separated portions of light received from the target. The image scanning apparatus is configured so that the central portion corresponds to an area of the target that is required to produce a high-quality image upon the TDI sensor. In order to fully scan a target using the TDI sensor a plurality of scanning movements 7 that are offset from each other in the y-direction may be required, i.e. a number of passes of the target may need to be made. The peripheral portion of a captured scan line, recorded by the detector array 190, may then be used for microscope operations that are not possible when solely using the TDI sensor 180, for example such as a focusing operation described below.

The operation of the image scanning apparatus 2 will now be explained in relation to FIGS. 4A to 4D and FIG. 5. FIGS. 4A to 4D illustrate an exemplary operation of TDI sensor 180. Typically, TDI sensor 180 is a high sensitivity, fast capture, monochromatic TDI sensor adapted to record light emitted due to the fluorescence of the target 30. Typically, this recorded light is of a narrow spectral bandwidth and any filtering that is required may be provided by an optional emission filter. However, other forms of TDI sensor may also be used with the present invention.

As described previously, a TDI sensor typically comprises a plurality of linear detection arrays. In the example shown in FIGS. 4A to 4D, the TDI sensor 180 comprises four detector arrays 210A to 210D. This number of arrays has been chosen as a simple example to explain the operation of the apparatus and in reality the number of parallel detector arrays may vary from one to a plurality of arrays. Each linear detection array 210 within the TDI sensor 180 is configured to record image information from the target 30 in the form of a scan line that corresponds to a spatial area of the target that is elongate in the y-direction. The TDI sensor 180 is then adapted to integrate image information from a number of different scan lines relating to a common spatial area of the target 30. This is equivalent to integrating image information, relating to a particular spatial area of the target 30, recorded over a number of predetermined time periods. In the present case this is achieved by capturing and integrating, within a TDI sensor scan sequence, four scan lines of a particular spatial area of the target.

Figure 4A:
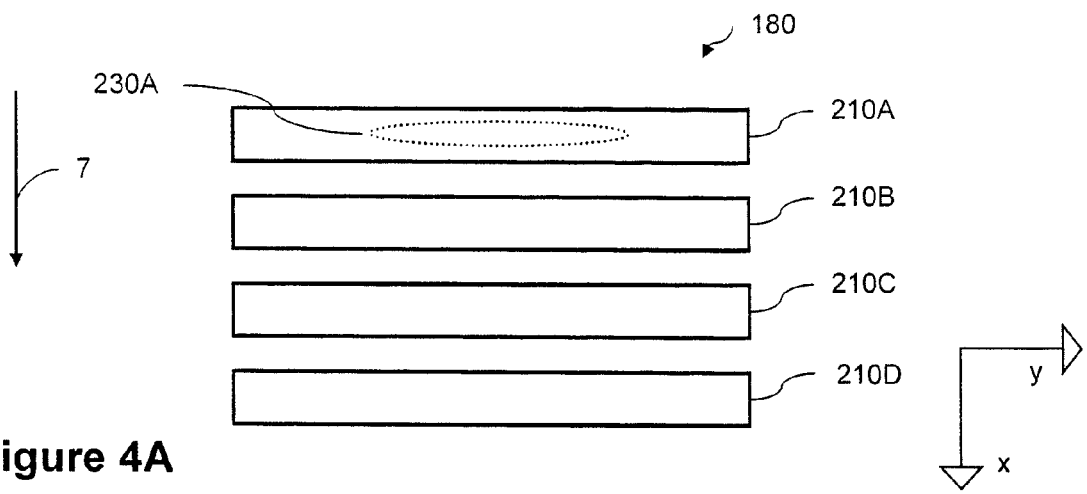
FIGS. 4A to 4D schematically illustrate the operation of an exemplary time integration delay sensor.
Figure 4B:
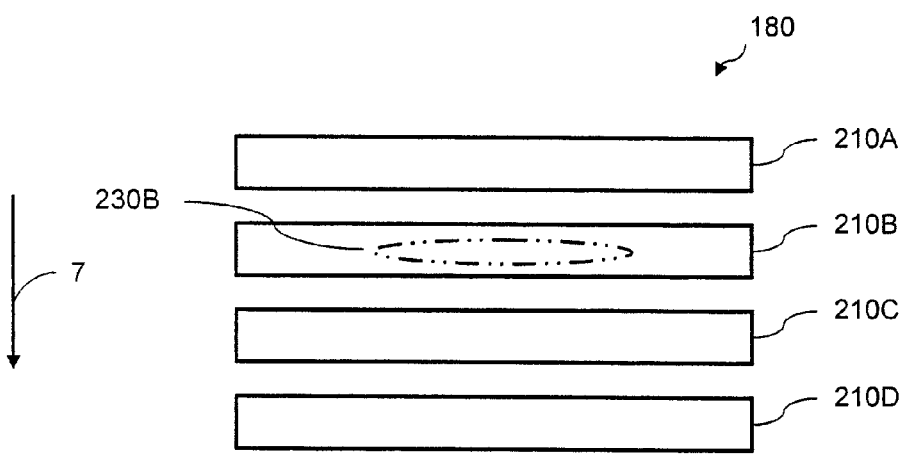

Before the capture of a particular scan line at step S505, the lens assembly 120 is typically positioned to effect a particular focus level. As before, this is performed by moving the lens assembly 120 in the z-direction. The lens assembly 120 is then held in a particular position in the z-direction for a short period while light from the target 30 is redirected through the image scanning apparatus 2 towards the TDI sensor 180. In FIG. 4A, the target 30 is positioned so that a first scan line or image 230A can be recorded on linear array 210A as described in step S505. This image 230A corresponds to a particular spatial area of the target 230. Typically, the amount of light emitted by the target 30 during fluorescence is weak and so the image 230A recorded by linear array 210A would also be weak (denoted by dashed lines).

After the first scan line 230A has been captured, the target 30 is moved in the x-direction at step S510 as part of scanning movement 7. At this point, the image information 230A recorded in the first detector array 210A is transferred to the second linear detector array 210B, typically by a charge transfer to the second array 210B. The first array 210A is then reset. In step S515, light from the same spatial area of the target 230 impinges on the array 210B and generates a second scan line or image 230B. This light generates additional charge within the array 210B, in effect integrating the image information from the first detector array 210A and the second detector array 210B.

Figure 4C:
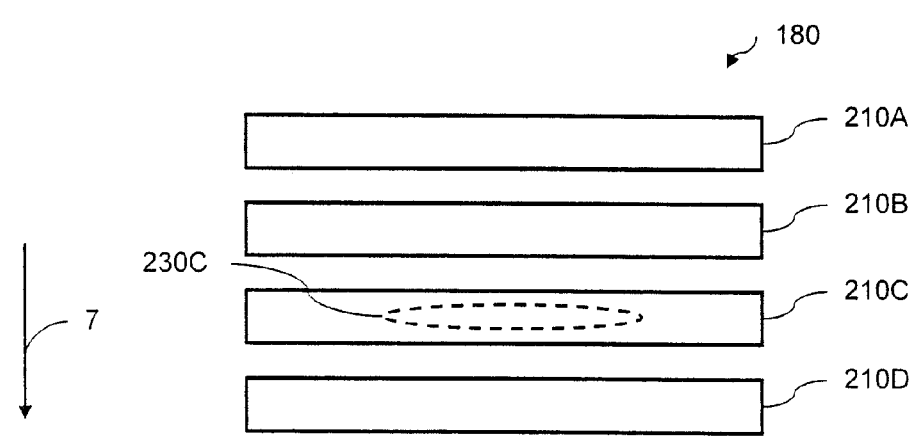
Figure 4D:
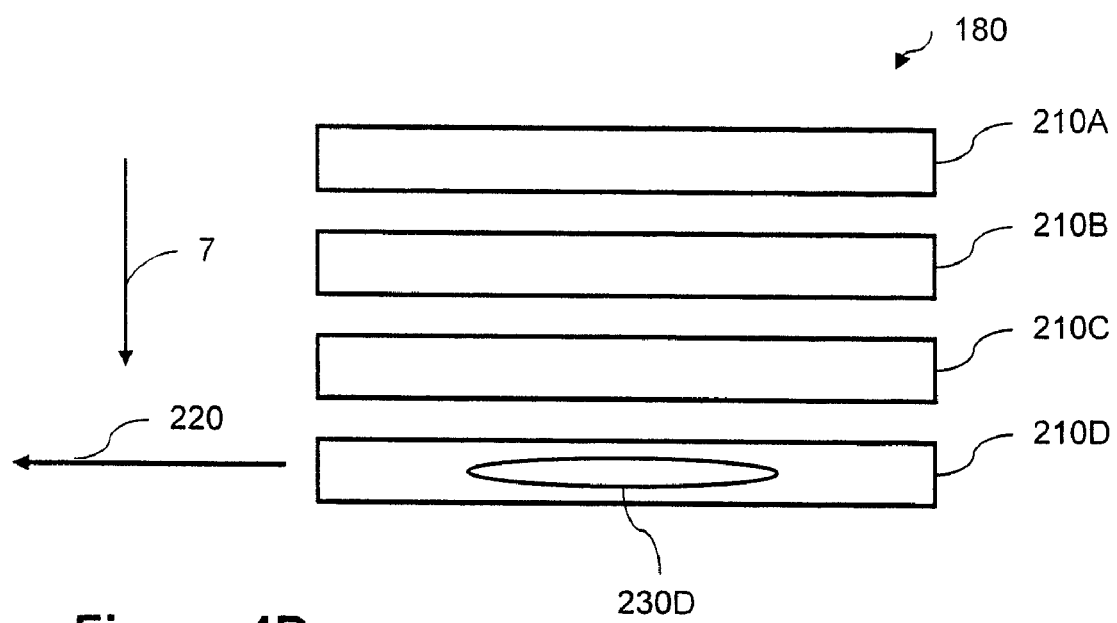

This process continues a third and fourth time in steps S520 and S525, and steps S530 and S535. In FIGS. 4C and 4D, additional image information 230C and 230D related to the spatial area of the target 230 is captured, further increasing the stored charge and providing a stronger image. Hence, by FIG. 4D, light from a particular area of the target 230 has been recorded and integrated four times by each of line detector arrays 210A to 210D, generating a strong image of the area of interest. After the fourth set of image information 230D is captured the stored charge is read out of the TDI sensor 180 at step S540, which is represented by arrow 220 in FIG. 4D. This then provides a single integrated scan line image.

During the process illustrated in FIGS. 4A to 4D, it is required to maintain an in-focus image of the target 30. This may be done in one of two ways.

Figure 5:
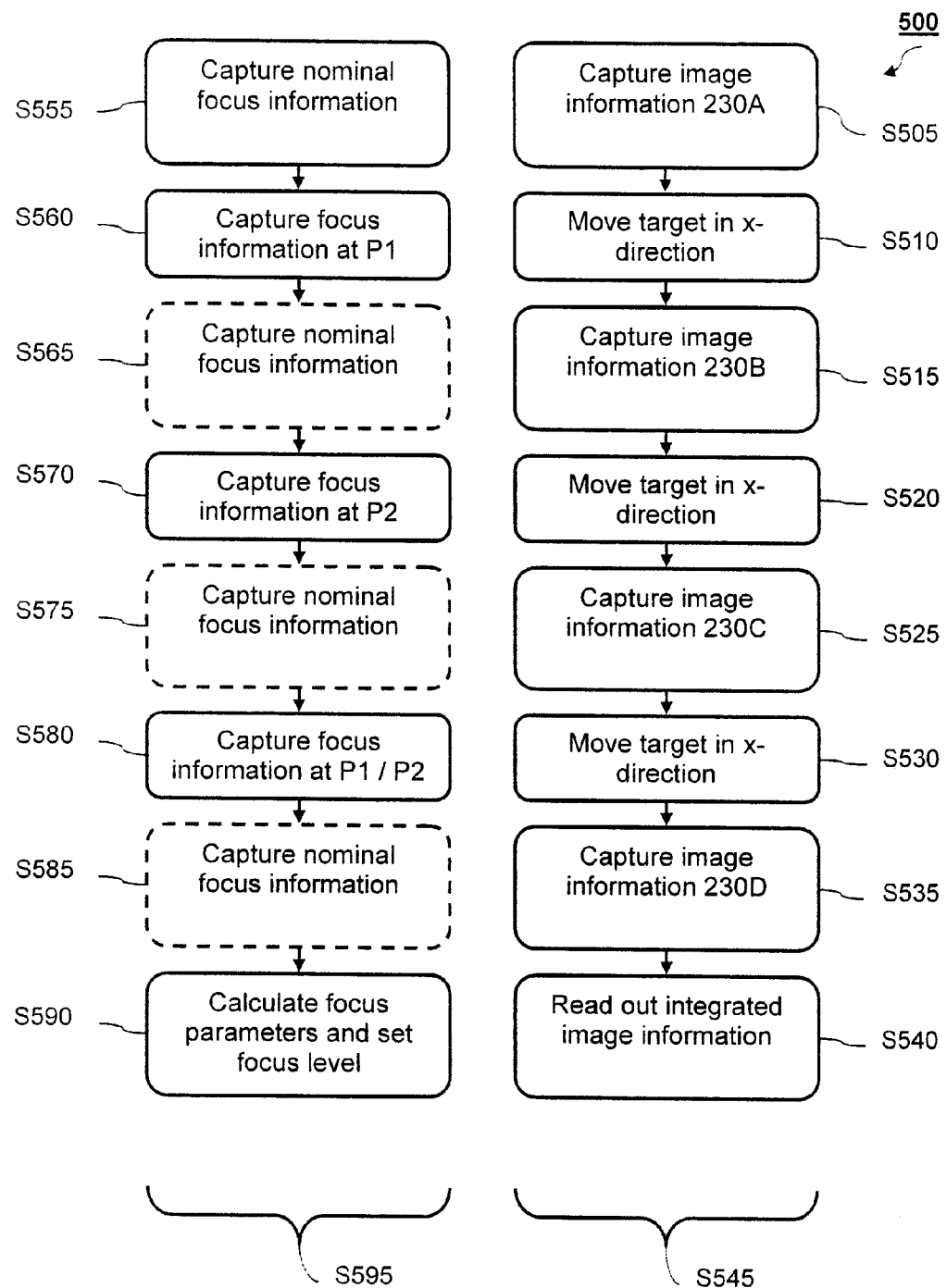
FIG. 5 is a flowchart illustrating an exemplary method of controlling the image scanning apparatus that may be used with any of the embodiments of the present invention.

The first method is illustrated in steps S595 of FIG. 5. This method uses a technique wherein a number of scan lines at different focus levels are recorded by detector arrays 190R, 190G and 190B during and/or between the capture of image information upon the TDI sensor 180, i.e. the image capture shown in FIGS. 4A to 4D.

Before the capture of image information in FIG. 4A the lens assembly is set to a pre-calculated or nominal focus position N, which may also be a default focus position. Whilst a scan line 230A is recorded by TDI sensor 180 at step S505, focus image information is recorded by the detector arrays 190 at step S555 using the peripheral portion of light information that impinges upon the detector array 190 after passing around light redirection device 130. This focus image information, captured in the RGB spectral band, is used as nominal focus information representative of a nominal focus level.

Whilst the target is moved in the scanning direction 7 at step S510 the lens 110 and/or lens assembly 120 is moved to a second focus position P1 that differs from the first or nominal focus position N. Typically, this second focus position corresponds to an out-of-focus position, either above or below the nominal focus position N by a distance d. At step S560 focus image information is captured by the detector arrays 190R, 190G and 190B at the second focus position using the peripheral portion of light. Depending on whether the scanning movement 7 has moved the target in the x-direction, this focus image information may correspond to the same spatial area of the target as the image information captured at the nominal focus position or may correspond to a different spatial area. The lens 110 and/or lens assembly is then returned to the nominal focus position in time to capture image information 230B at step S515.

During the subsequent capture of image information 230B at step S515 the focusing method may be configured to capture further image information at the nominal focus position at step S565. Due to the scanning movement 7 this will represent image information from a different spatial area of the target. This additional capture is optional (as denoted by the dashed lines), however the more focus data that is captured the more accurate the in-focus position estimate will be. At step S570, during further scanning movement 7 in the x-direction, another out-of-focus scan line image may be captured by the detector array 190. This focus image information may be captured at the same focus position as step S560 or at a different focus position to both the nominal focus position N and the first out-of-focus position P1. For example, if the second focus position P1 corresponds to an out-of-focus position above the nominal focus position N, a third focus position P2 may correspond to an out-of-focus position a distance d below the nominal focus position N. P1 and P2 need not be symmetric and the distances above and below the nominal focus need not be equal. Capturing focus image information at a plurality of focus positions increases the accuracy of an in-focus position estimate. At steps S575 and S585 further nominal focus image information may be captured in a similar manner to steps S555 and S565. At step S580 further out-of-focus image information may be gathered at one or more of positions P1 and P2. A graph illustrating the change in focus positions during a scanning movement 7 is shown in FIG. 6.

The image information recorded at these one or more further focus levels is then used together with the focus image information recorded at the nominal focus position to calculate one or more focus parameters. In the present example these focus parameters comprise a focus merit value; such a value provides a numerical value which is dependent upon the amount of fine detail within the image information. These focus parameters are then used to calculate an in-focus position common to the areas of the target being recorded by the TDI sensor 180.

Figure 6:
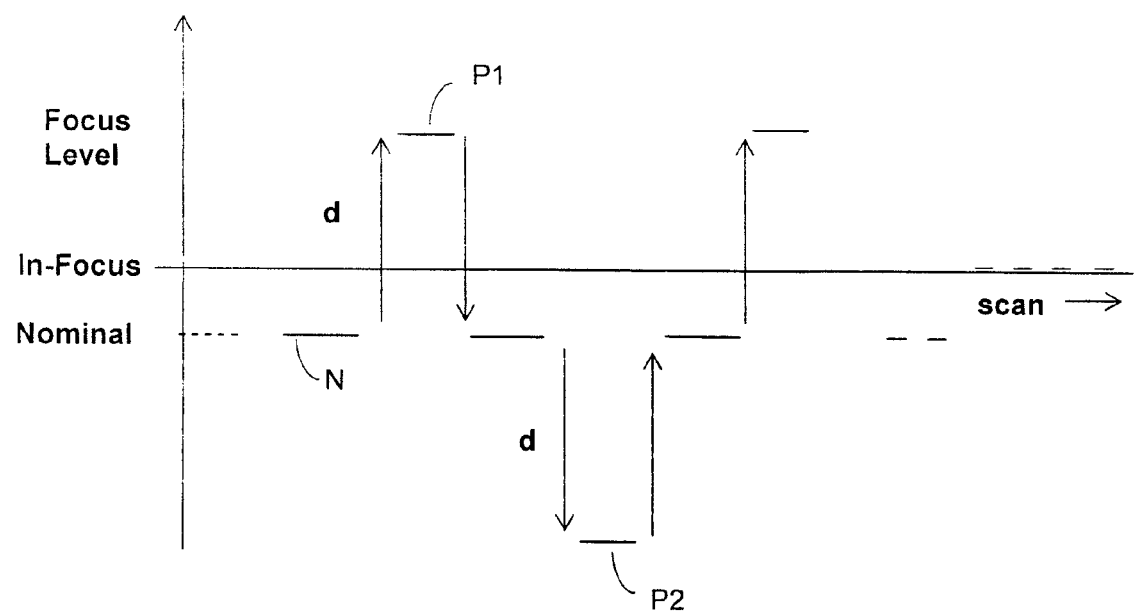
FIG. 6 is a graph illustrating an exemplary focusing operation that may be used with any of the embodiments of the present invention.
Figure 7:
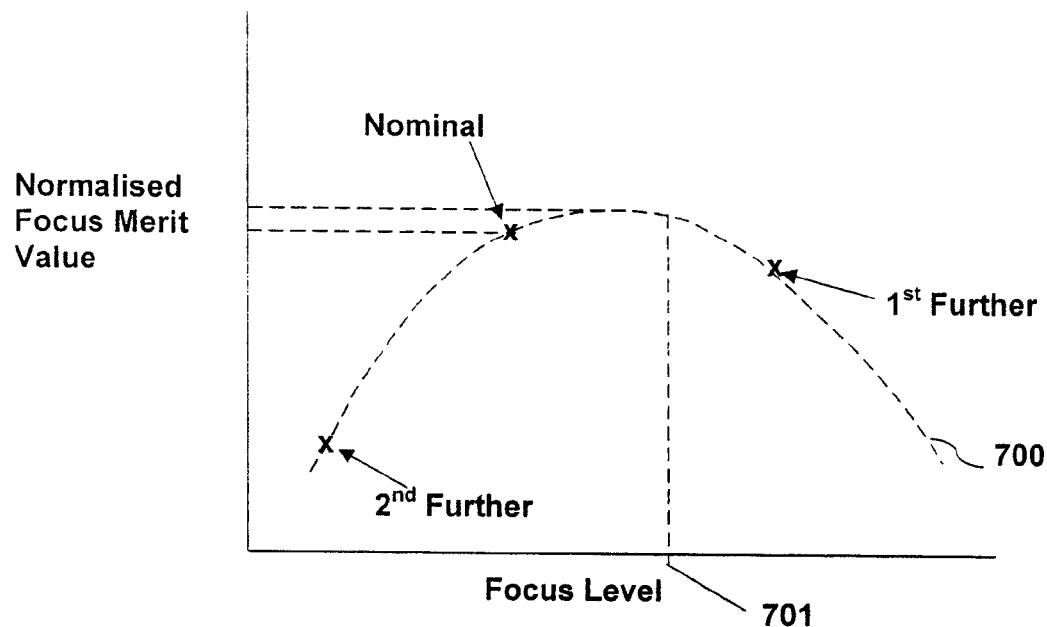
FIG. 7 is a second graph illustrating a method of calculating an in-focus position that may be used with any of the embodiments of the present invention.

Referring to FIG. 6, it can be seen that the in-focus level is positioned on the first further focus level side of the nominal focus level. Ideally, we wish for the nominal focus level to coincide with the in-focus level and thereby obtain the best image information. In order to determine the position of the in-focus level the focus merit values for the nominal N and first P1 and second P2 further focus levels are fitted to a curve at step S590. An example of such a curve is shown in FIG. 7, this being plotted on a graph of focus parameter (ordinate) in the form of normalised focus merit values, against focus level (abscissa). When a focus merit curve of known general form (illustrated at 700) is fitted to the normalised focus merit values, it becomes clear that the nominal focus position is the nearest to the peak (representing the in-focus position 701). The intersection of the peak position on the abscissa axis gives the focus level of the in-focus position.

This in-focus position can be used by a processor connected to the image scanning apparatus 2 to move the lens assembly 120 to a desired focus position before step S505 in sequence S545. This process may be performed while the target 30 is being moved to the next scan line in the x-direction during scanning motion 7 after or during step S540. Further details of a method of calculating a focus position are provided in US Patent Publication 2006/0238847. which is incorporated herein by reference.

In alternative embodiments of the present invention the focusing steps S595 may be performed during a plurality of repetitions of steps S545, for example focus data may be obtained in the manner of steps S595 during three cycles of steps S545 whilst three complete integrated scan lines are captured using TDI sensor 180. Alternatively, steps S560, S570 and S580 may be performed at other times during cycle S545 at points where image information is not captured by the TDI sensor 180. Additionally, image information from one or more of detector arrays 190R, 190G and 190B may be used in the method, as opposed to RGB image information from the three arrays combined.

Returning to FIG. 5, steps S545 and S595, representing the operation of the TDI sensor 180 and the detector array 190 respectively, may be synchronized or performed independently of each other. In certain embodiments the detector array 190 is entirely independent of the TDI sensor 180. Such an arrangement is advantageous as one of the TDI sensor system or the detector array system may be modified without affecting the other.

In order to simplify the analysis of the TDI sensor 180, the operation of the TDI sensor 180 was described in relation to a single scan line. In true operation, at any one time, the TDI sensor 180 will capture image information from different areas of the target 30 in parallel using each of arrays 210A to 210D, i.e. at any one time the TDI sensor is capturing image information relating to an area of the target m pixels in width, wherein, in the present example, m=4. For example, after charge has been transferred from array 210A to array 210B, array 210A will then capture image information relating to a further area of the target in parallel with array 210B.

The second method of using detector array 190 to generate focus data comprises using the detector arrays 190 to build a focus map of the target 30 before an image of the fluorescing target is captured by TDI sensor 180. In this case, the detector array 190 is adapted to capture a portion of the light from the target 30 that is separated in time from the portion of light captured by the TDI sensor 180. A focus map may be built using the peripheral portion of image information that bypasses light redirection device 130 or the redirection device may be temporarily removed from the optical path that ends with the detector array 190. A focus map of the target 30 is typically generated by scanning the target at a number of different focus positions, applying similar methods to the first focusing method, and then calculating an optimum in focus position for the TDI sensor scan during the captured RGB focus data. In other focus map methods a plurality of "z-stack" images, corresponding to different focus levels, are generated and used to calculate an optimum focus position at a variety of x locations that may be used by a focus processor to fix a focus level at a particular location. US Patent publication number US2004/0256538A1 or EP Patent Publication number EP-A-1610166, both incorporated herein by reference, disclose suitable methods of creating a focus map. In these cases, the focal map is generated using the RGB detector arrays 190 rather than the TDI sensor 180 and so the focusing operations do not interfere with the capture of fluorescent information using the sensor.

Figure 3:
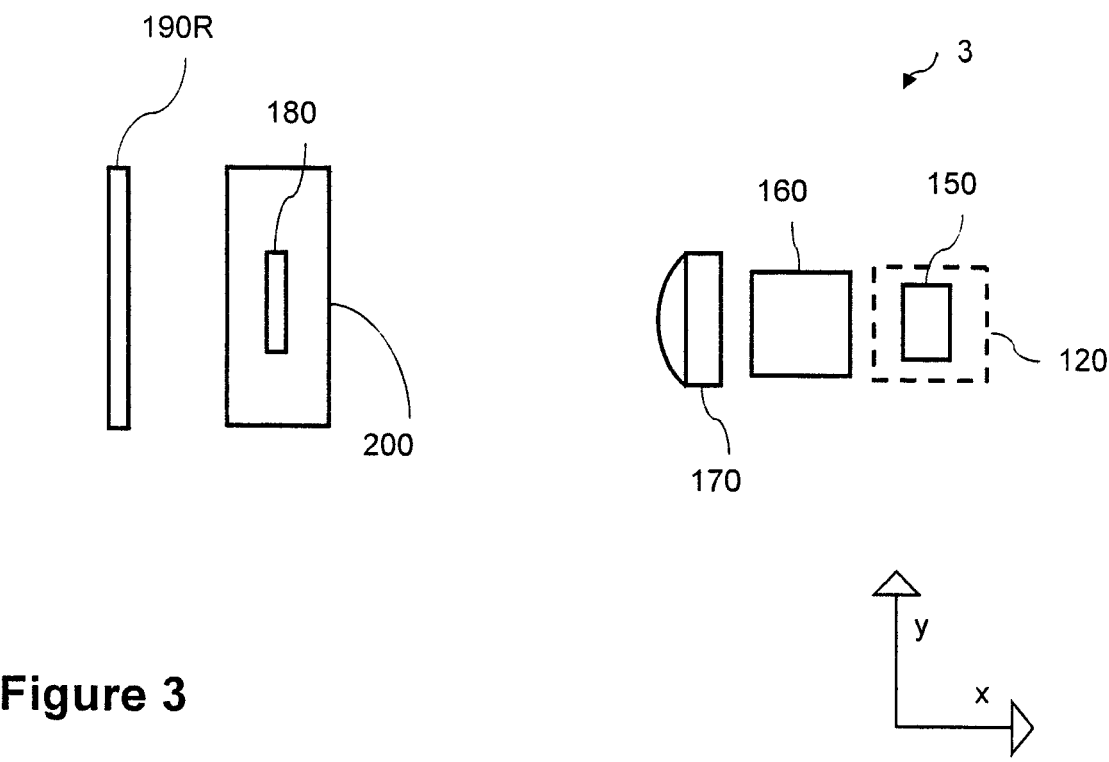
FIG. 3 is a plan of an exemplary image scanning apparatus according to a second embodiment of the present invention.

A second embodiment of the present invention is shown in FIG. 3 and comprises a variant of the light redirection device 130. In this embodiment, light redirection device 130 comprises a dichroic beam splitter 200 that extends across the length of linear detector arrays 190. In this case, dichroic splitter 200 is adapted to direct light of the second wavelength or spectral band emitted from the target 30 to the TDI sensor 180 but then to allow light of one or more of the red, green and blue spectral bands to pass through the dichroic beam splitter 200 to one or more of the RGB detector arrays 190R, 190G and 190B. In this case, an RGB image can be captured in parallel with the capture of a high quality fluorescent image captured by the TDI sensor 180. Hence, the detector array 190 receives a portion of light from the target that is chromatically or spectrally distinct from the light received from the target by the TDI sensor 180. An in-focus position calculation may be performed using this embodiment in a similar manner to method 500, wherein the second image information recorded by the detector arrays 190 would comprise a complete scan line of differing spectral intensity to the image information captured by the TDI sensor 180.

Figure 8:
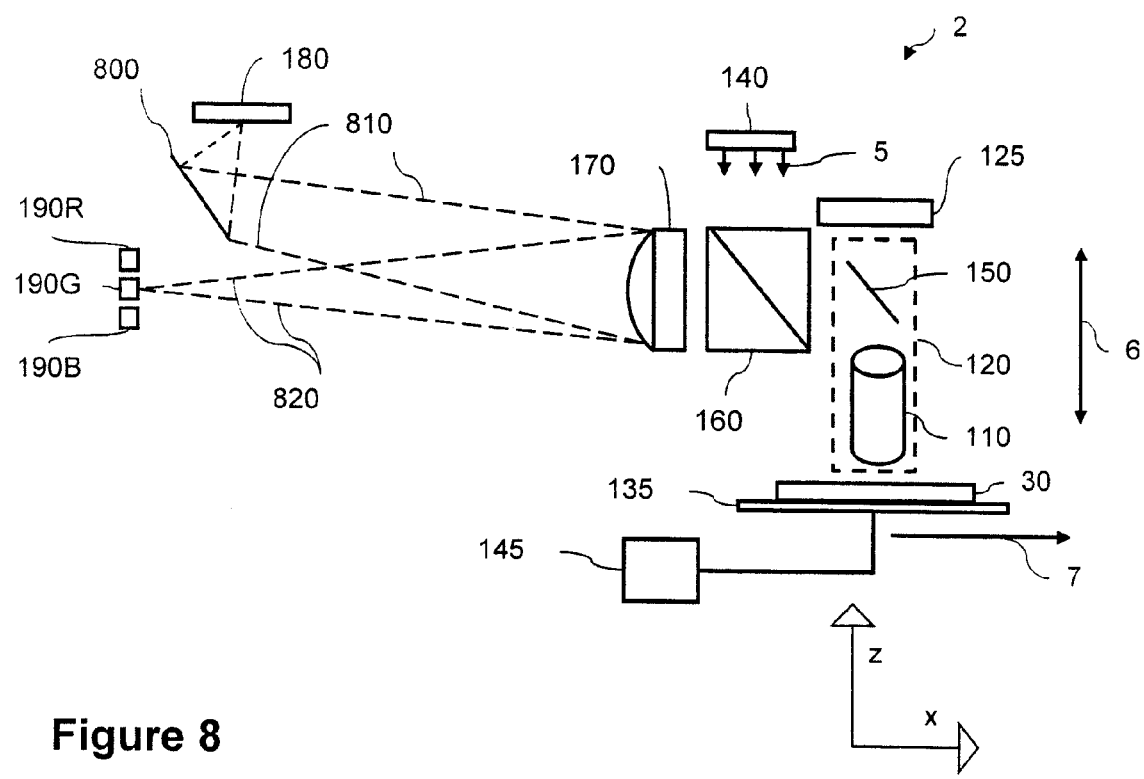
FIG. 8 is a schematic side view of an exemplary image scanning apparatus according to a third embodiment of the present invention; and, FIG. 9 is a schematic side view of an exemplary image scanning apparatus according to a fourth embodiment of the present invention.

A third embodiment of the present invention is shown in FIG. 8 and is a variation of either the first or second embodiments described above. In this embodiment the light redirection device 800 comprises an off-axis mirror and is aligned so that the light 810 that reaches the TDI sensor 180 arises from a first area of the target 30 and this light 810 differs from light 820 that reaches the detector array 190, as light 820 arises from a second area of the target. The mirror 800 is described as being "off-axis" as it is removed from the optical path or "axis" of the light 820 that is directed towards the detector array 190. In the present case the off axis distance may be between 1 and 20 millimeters in the z-direction. For example, using such an arrangement the light 810 received by the TDI sensor would correspond to a first set of scan lines and the light 820 received concurrently by the detector array 190 would then correspond to a second set of scan lines that are separated in the x direction from the first set of scan lines (wherein each set of scan lines may comprise one or more scan lines). The methods of controlling the focus of the image scanning apparatus may be adapted to operate using the third embodiment, as the remaining apparatus is identical to that used in the first and second embodiments. Variations of the third embodiment include a first variation wherein the TDI sensor 180 is located above the detector array 190 and the light redirection direction is omitted. In this variation the TDI sensor 180 is aligned parallel to the detector array 190. In a second variation the positions of the TDI sensor 180 and the detector array 90 may be exchanged.

The present invention provides the advantage of enabling an image of a fluorescing target to stay in-focus, whilst still enabling rapid image scan times. When using the focus method described with relation to FIG. 5, an optimum infocus image of a target may be maintained during a scanning movement without requiring a time-consuming initial focus scan of the target. In this manner, focusing techniques designed to be used with a RGB line-scan image apparatus may also be used in fluorescence microscopy.

Figure 9:
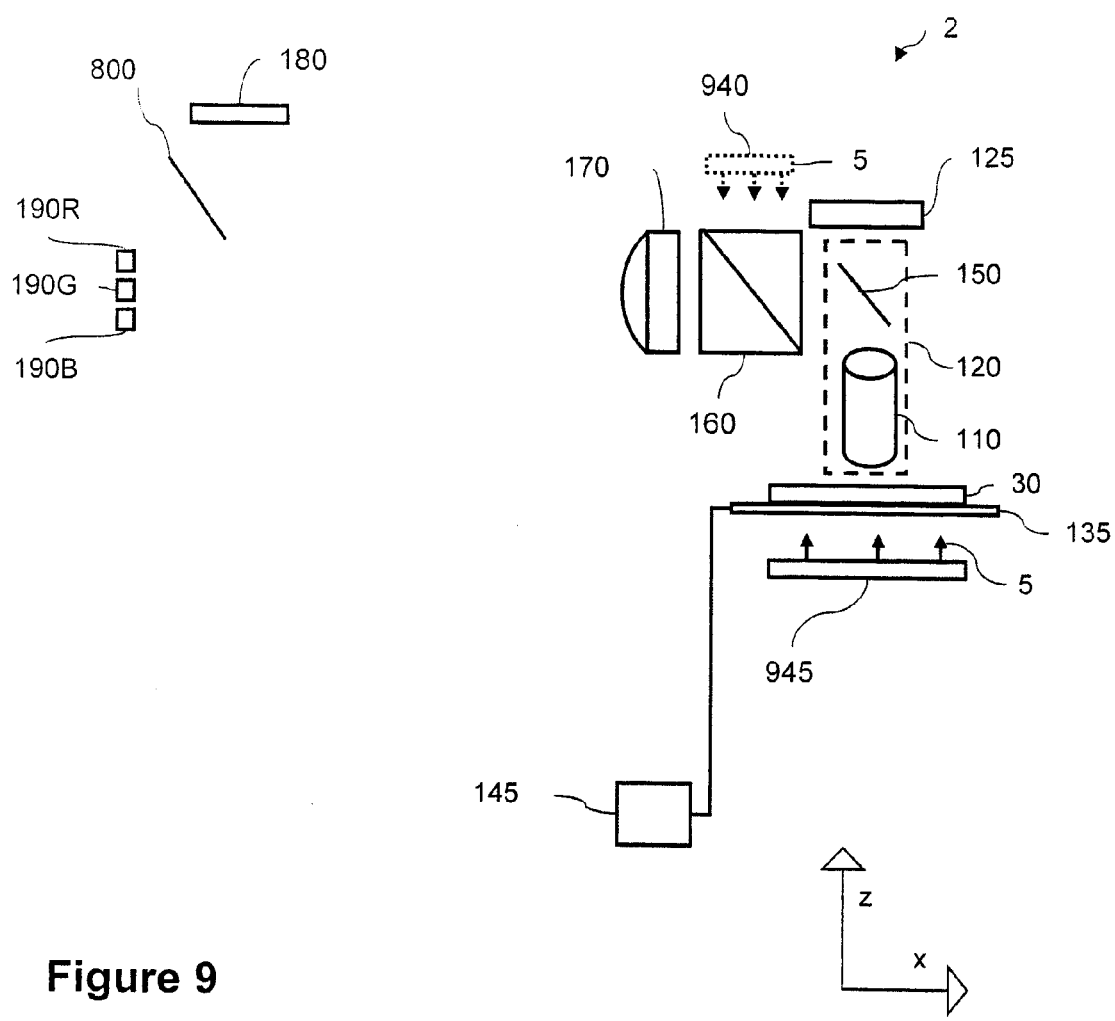

A fourth embodiment of the present invention is shown in FIG. 9. The fourth embodiment comprises a modified illumination system for illuminating the target 30. This modified illumination system may also be used with the first and second embodiments and is not limited to use with the third embodiment as shown in FIG. 9.

The modified illumination system is adapted to increase efficiency of the detector array 190 independently of the processes involved in capturing fluorescence image information and comprises an illumination or exciter source 945 located below the target 30. Light emitted from the illumination source 945 passes upward towards the target 30, where some of the emitted light is absorbed by the sample. Different parts of the target 30 absorb different amounts of emitted light and thus generate the contrast in a captured image. This technique is known in the art as trans-illumination. This technique differs from the reflective or "epi" illumination method shown in FIG. 2A, wherein light from an exciter source 140 above the target 30 irradiates the target and, independent of the fluorescence, is reflected, or scattered, back from the target to be eventually received by the detector array 190.

Trans-illumination enables more light to reach the detector array 190 from transmissive areas of the sample and thus increases the contrast between light and dark areas when compared to epi-illumination. This then leads to a greater signal-to-noise ratio for the image captured by the detector array 190 and may increase the accuracy of the focusing operations. If trans-illumination is only performed using light within the exciter radiation wavebands then such light will be filtered before reaching the TDI sensor 180. This means that the use of trans-illumination to generate a higher contrast focus image will not affect the image recorded by the TDI sensor. The efficiency of the illumination system may thus be increased by, on average an order of magnitude with no detrimental effect.

It is also possible to use an epi-illumination source as well as the trans-illumination source 945; optional epi-illumination source 940 is shown using dashed lines in FIG. 9. Epi-illumination may sometimes be required for samples that are not translucent or transparent or to increase the overall illumination efficiency of the image scanning apparatus 9.

I claim:

1. An image scanning apparatus comprising: a time delay integration sensor for obtaining first image information from a target; and a scan device for causing relative motion between the time delay integration sensor and the target to enable an image of the target to be generated from a scan of the target; and a processor; the image scanning apparatus characterized by: a detector array for obtaining second image information from a target; wherein the first image information corresponds to a first portion of light received from first area of the target and the second image information corresponds to a second portion of light received from a second area of the target, the first and second areas of the target being different from each other; and wherein the processor is adapted to use said second information to calculate a focus position for obtaining the first image information.

2. The image scanning apparatus of claim 1, wherein the first and second portions further respectively correspond to:
different wavelengths of light received from the target.

3. The image scanning apparatus of claim 1, further comprising:
a focusing device adapted to modify the focus between the time delay integration sensor and the target;
wherein the processor is adapted to control the focusing device and the second image information is used by the processor to select a focus position for the focusing device.

4. The image scanning apparatus of claim 1, further comprising a fluorescence exciter source configured to irradiate the target and cause the target to fluoresce.

5. The image scanning apparatus of claim 4, wherein the exciter source comprises an ultra violet source.

6. The image scanning apparatus of claim 4, wherein the exciter source is located below the sample to provide trans-illumination.

7. The image scanning apparatus of claim 6, further comprising a filter positioned on the optical path between the target and the time delay integration sensor adapted to prevent predetermined spectral bands of radiation from impinging on the time delay integration sensor.

8. The image scanning apparatus of claim 1, wherein the optical path length from the target to the detector array equals the optical path length from the target to the time delay integration sensor.

9. The image scanning apparatus of claim 4, wherein the detector array comprises a red, green, blue (RGB) detector array.

10. The image scanning apparatus of claim 1, further comprising at least one light redirection device configured to redirect light from the target to at least one of the time delay integration sensor and the detector array.

11. The image scanning apparatus of claim 10, wherein the at least one light redirection device comprises a dichroic beam splitter.

12. The image scanning apparatus of claim 10, wherein the at least one light redirection device comprises a mirror positioned along the optical path between the target and the detector array such that a central portion of the light received from the target is directed toward the time delay integration sensor and a peripheral portion of the light received from the target is directed toward the detector array.

13. The image scanning apparatus of claim 10, wherein the light redirection device comprises an off-axis mirror, located a predetermined distance from an optical path upon which light is received by one of the time delay integration sensor or the detector array, so as to concurrently redirect light to the other of the detector array or time delay integration sensor.

14. The image scanning apparatus of claim 1, further comprising at least one light source adapted to illuminate the target using at least one of epi-illumination or trans-illumination.

15. The image scanning apparatus of claim 1, wherein the detector array is a linear detector array configured to capture a scan line of the target.

16. The image scanning apparatus of claim 1, wherein the second image information comprises out of focus image information and the detector array is controlled so as to obtain such information during a period in which the time delay integration sensor does not capture first image information.

17. The image scanning apparatus of claim 16, wherein the detector array is controlled so as to obtain third image information comprising focused image information during a period in which the time delay integration sensor obtains first image information.

18. The image scanning apparatus of claim 17, wherein the third image information is also used together with the second image information to calculate a focus position for obtaining the first image information.

19. A method of focusing an image scanning apparatus comprising: capturing first image information of a target using a time delay integration sensor, the first image information corresponding to a first portion of light received from a first area of the target that is used to generate an image of the target; capturing second image information of the target using a detector array, the second image information corresponding to a second portion of light received from a second area of the target the first and second areas of the target being different from each other; calculating a focus position for use in capturing the first image information using the second image information; and adjusting the focus of the image scanning apparatus according to the calculated focus position; generating relative motion between the time delay integration sensor and the target before capturing further first image information at the calculated focus position, the further first image information corresponding to light received from a further part of the target.

20. The method of claim 19, wherein the first and second portions are further separated chromatically.

21. The method of claim 19, wherein capturing first image information further comprises:

irradiating the target to enable the target to fluoresce; and the first image information comprises image information corresponding to the fluorescence of the target.

22. The method of claim 19, wherein the second image information comprises out of focus image information and such information is captured during a period in which the time delay integration sensor does not capture first image information.

23. The method of claim 22, further comprising capturing third image information of the target using the detector array comprising focused image information during a period in which the time delay integration sensor captures first image information.

24. The method of claim 23, wherein the third image information is used together with the second image information to calculate a focus position for obtaining the first image information.

* * * * *